(12) United States Patent
Addison et al.

(10) Patent No.: US 12,295,754 B2
(45) Date of Patent: *May 13, 2025

(54) DESATURATION SEVERITY PREDICTION AND ALARM MANAGEMENT

(71) Applicant: Covidien LP, Mansfield, MA (US)

(72) Inventors: Paul S. Addison, Edinburgh (GB); Philip Smit, Hamilton (GB); André Antunes, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/419,478

(22) Filed: Jan. 22, 2024

(65) Prior Publication Data
US 2024/0188898 A1    Jun. 13, 2024

Related U.S. Application Data

(63) Continuation of application No. 18/052,516, filed on Nov. 3, 2022, now Pat. No. 11,877,868, which is a
(Continued)

(51) Int. Cl.
| | |
|---|---|
| A61B 5/00 | (2006.01) |
| A61B 5/1455 | (2006.01) |
| G06N 3/08 | (2023.01) |
| G08B 21/18 | (2006.01) |
| G08B 29/20 | (2006.01) |
| G16H 50/30 | (2018.01) |

(52) U.S. Cl.
CPC ........ *A61B 5/7275* (2013.01); *A61B 5/14552* (2013.01); *A61B 5/7264* (2013.01); *A61B 5/7282* (2013.01); *A61B 5/746* (2013.01); *G06N 3/08* (2013.01); *G08B 21/182* (2013.01); *G08B 29/20* (2013.01); *G16H 50/30* (2018.01); *A61B 5/0022* (2013.01); *A61B 5/6826* (2013.01)

(58) Field of Classification Search
CPC . A61B 5/7275; A61B 5/14552; A61B 5/7264; A61B 5/7282; A61B 5/746; G16H 50/30; G06N 3/08; G08B 21/182; G08B 29/20
USPC ........................................................ 600/324
See application file for complete search history.

(56) References Cited

U.S. PATENT DOCUMENTS

| | | | | |
|---|---|---|---|---|
| 5,520,176 A | * | 5/1996 | Cohen .................. | A61B 5/4806 600/300 |
| 11,504,072 B2 | * | 11/2022 | Addison .................. | G06N 3/08 |

(Continued)

*Primary Examiner* — Kerri L McNally
(74) *Attorney, Agent, or Firm* — Draft Masters IP, LLC (57) ABSTRACT

Implementations described herein disclose a method of classifying oxygen level desaturation events. In one implementation, the method includes receiving input signal sequences, the input signals indicative of a physiological condition of a patient, generating an input sequence of oxygen saturation levels based on the input signal sequence, comparing the input sequence of oxygen saturation levels to a desaturation alarm threshold to determine a desaturation event, generating an input feature matrix based on at least one of the input signal sequences and the input sequence of oxygen saturation levels, and classifying based on the input feature matrix, using a neural network, the desaturation event being a severe desaturation event (SDE) or a non-severe desaturation event (non-SDE).

20 Claims, 7 Drawing Sheets

Related U.S. Application Data continuation of application No. 16/854,089, filed on Apr. 21, 2020, now Pat. No. 11,504,072.

(56) References Cited

U.S. PATENT DOCUMENTS

| | | | |
|---|---|---|---|
| 11,877,868 B2* | 1/2024 | Addison | G06N 3/044 |
| 2002/0165462 A1* | 11/2002 | Westbrook | A61B 5/7275 |
| | | | 600/529 |
| 2005/0131283 A1* | 6/2005 | Grant | A61B 5/08 |
| | | | 600/323 |
| 2008/0221418 A1* | 9/2008 | Al-Ali | A61B 5/02416 |
| | | | 600/324 |
| 2011/0295083 A1* | 12/2011 | Doelling | A61B 5/11 |
| | | | 600/407 |
| 2012/0253142 A1* | 10/2012 | Meger | A61B 5/7221 |
| | | | 600/301 |
| 2015/0094962 A1* | 4/2015 | Hoegh | G16H 50/30 |
| | | | 702/19 |
| 2017/0296104 A1 | 10/2017 | Ryan et al. | |
| 2018/0015282 A1* | 1/2018 | Waner | A61B 5/00 |
| 2018/0353126 A1* | 12/2018 | Gozal | A61B 5/14551 |
| 2018/0353718 A1 | 12/2018 | Gale et al. | |
| 2019/0154660 A1* | 5/2019 | Cafferty | G01N 21/3151 |

* cited by examiner

DESATURATION SEVERITY PREDICTION AND ALARM MANAGEMENT

CROSS-REFERENCE TO RELATED APPLICATIONS

The present application is a continuation application of U.S. application Ser. No. 18/052,516 filed Nov. 3, 2022, entitled "DESATURATION SEVERITY PREDICTION AND ALARM MANAGEMENT", which is a continuation application of U.S. application Ser. No. 16/854,089 filed Apr. 21, 2020, entitled "DESATURATION SEVERITY PREDICTION AND ALARM MANAGEMENT" and issued as U.S. Pat. No. 11,504,072 B2, all of which are specifically incorporated by reference herein for all that they disclose or teach.

BACKGROUND

Biomedical monitoring devices such as pulse oximeters, glucose sensors, electrocardiograms, capnometers, fetal monitors, electromyograms, electroencephalograms, ultrasounds, etc., may provide lagging indicators of physiological phenomena. In other words, these devices generally provide a signal or a series of signals that are indicative of a patient condition that has already occurred. For example, a pulse oximeter is a small, clip-like device that attaches to a body part, like toes or an earlobe. It's most commonly put on a finger to measure how well a patient's heart is pumping oxygen through the body by determining the oxygen content of arterial blood. However, while the oxygen level provides an indication of various conditions such as hypoxemia, low cardiac output, tissue perfusion issues, the oxygen saturation level determined by a pulse oximeter is a lagging indicator that may be indicative of the physiological condition causing such saturation level.

SUMMARY

Implementations described herein disclose a method of classifying oxygen level desaturation events. In one implementation, the method includes receiving input signal sequences, the input signals indicative of a physiological condition of a patient, generating an input sequence of oxygen saturation levels based on the input signal sequence, comparing the input sequence of oxygen saturation levels to a desaturation alarm threshold to determine a desaturation event, generating input feature matrices based on at least one of the input signal sequences and the input sequence of oxygen saturation levels, and classifying based on the input feature matrix, using a neural network, the desaturation event being a severe desaturation event (SDE) or a non-severe desaturation event (non-SDE).

In an alternative implementation, classifying the desaturation event further includes inputting the input feature matrix to the neural network, predicting a length of the desaturation event using the neural network, and classifying the desaturation event based on the predicted length of the desaturation event. Alternatively, classifying the desaturation event further includes inputting the input feature matrix to the neural network, predicting a depth of the desaturation event using the neural network, and classifying the desaturation event based on the predicted length of the desaturation event. Alternatively, the method further includes reducing an alarm delay in response to classifying the desaturation event being an SDE.

In an alternative implementation, the method further includes increasing an alarm delay in response to classifying the desaturation event being a non-SDE. Alternatively, the method further includes generating, based on the input feature matrix and using the neural network, probability associated with the desaturation event being SDE or non-SDE. Yet alternatively, the method further includes comparing the probability associated with the desaturation event being SDE or non-SDE with a threshold probability and adjusting the alarm delay in response to the comparison. Alternatively, adjusting the alarm delay further comprises adjusting the alarm delay based on the alarm delay as a non-linear function of the probability associated with the desaturation event. In one implementation, the neural network is at least one of a convolutional neural network (CNN) and a long short-term memory (LSTM) neural network. Alternatively, the input feature matrix is one of a matrix of maximum slopes of PPG pulses, a matrix of steepness of PPG pulses, a matrix of normalized amplitudes of PPG pulses, a matrix of maximum curvatures of PPG pulses, and a matrix of maximum negative slopes before dicrotic notches of PPG pulses.

In a computing environment, a method performed at least in part on at least one processor, the method including receiving input signal sequences, the input signals indicative of a physiological condition of a patient, generating an input sequence of oxygen saturation levels based on the input signal sequences, comparing the input sequence of oxygen saturation levels to a desaturation alarm threshold to determine a desaturation event, generating an input feature matrix based on at least one of the input signal sequences and the input sequence of oxygen saturation levels, classifying, based on the input feature matrix and using a neural network, the desaturation event being a severe desaturation event (SDE) or a non-severe desaturation event (non-SDE), and adjusting an alarm delay in response to classifying the desaturation event being an SDE or a non-SDE.

A physical article of manufacture including one or more tangible computer-readable storage media, encoding computer-executable instructions for executing on a computer system a computer process to provide an automated connection to a collaboration event for a computing device, the computer process including receiving input signal sequences, the input signals indicative of a physiological condition of a patient, generating an input sequence of oxygen saturation levels based on the input signal sequences, comparing the input sequence of oxygen saturation levels to a desaturation alarm threshold to determine a desaturation event, generating an input feature matrix based on at least one of the input signal sequences and the input sequence of oxygen saturation levels, classifying, based on the input feature matrix and using a neural network, the desaturation event being a severe desaturation event (SDE) or a non-severe desaturation event (non-SDE), and adjusting an alarm delay in response to classifying the desaturation event being an SDE or a non-SDE.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

A further understanding of the nature and advantages of the present technology may be realized by reference to the figures, which are described in the remaining portion of the specification.

DETAILED DESCRIPTIONS

Hypoxemia is a condition that indicates lower than normal concentration of oxygen levels in arterial blood of a patient. Hypoxemia may result in hypoxia or hypoxic condition for the patient, characterized by inadequate oxygen content in patient tissues. Pulse oximeters may be used to measure the oxygen content of arterial blood to indicate existing hypoxia condition as well as to predict impending hypoxia. A clinician may want to be alerted when oxygen saturation level in arterial blood dips below a threshold, indicating an oxygen level desaturation event.

However, in some circumstances such a desaturation event may be trivial in that the oxygen saturation level may dip below the threshold only for a short period—such as a few seconds. Such short desaturation event may not warrant generating an alarm to notify the clinician. Similarly, in other circumstances, the desaturation event may be trivial in the sense that even when it is for a longer time period, the saturation levels may not have dipped significantly below the threshold, in which case, even if such event may warrant an alarm, the alarm generation may be delayed.

On the other hand, the desaturation event may be serious in that the oxygen saturation level may dip below the threshold for a prolonged period and/or significantly below the threshold level. The technology disclosed herein provides a method for alarm management based on predicted severity of oxygen level desaturation events. Specifically, the method and system disclosed herein may use artificial intelligence (AI) based alarm management where neural network (NN) models may be used to predict the probability of a severe desaturation event (SDE) or a non-severe desaturation event (non-SDE).

For example, a deep learning model may be trained to determine the severity of a desaturation event as the desaturation threshold is reached. The severity may, for example, be determined by the predicted depth of the desaturation event, the predicted time spent below the saturation threshold, or a combination of both.

Figure 1:
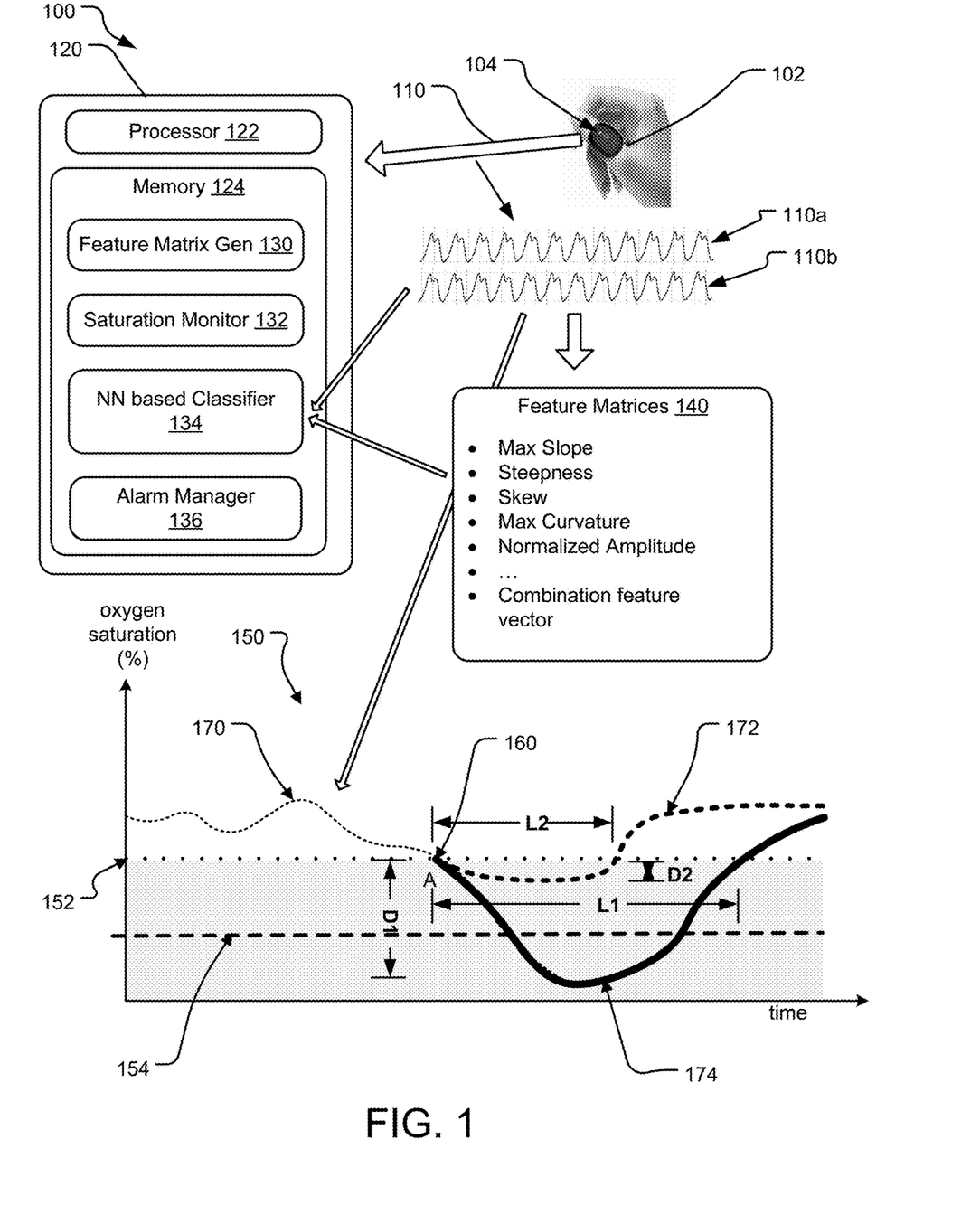
FIG. 1 illustrates an example schematic view of oxygen level desaturation severity prediction system for a patient as disclosed herein.

FIG. 1 illustrates an example schematic view of oxygen level desaturation severity prediction system 100 for a patient 102. A pulse oximeter 104 may be used to measure the oxygen saturation ($SpO_2$) level in the patient. For example, the pulse oximeter 104 may be attached to the patient's thumb. The pulse oximeter 104 may be communicatively connected to a computing system 120. For example, the pulse oximeter 104 may be connected to the computing system 120 wirelessly and it may send a sequence of input signals 110 measured by the oximeter 104 over a period of time. For example, such input signal sequence 110 may be communicated at every second. In one implementation, the input signal sequence 110 may include photoplethysmographic (PPG) signals such as a red signal 110a, an infrared signal 110b, etc. The pulse oximeter 104 may also use the values of the red signal 110a and the infrared signal 110b, to generate values of oxygen saturation levels (the $SpO_2$ levels). A sequence of such $SpO_2$ levels generated by the pulse oximeter 104 is illustrated by a sequence of oxygen saturation levels 170.

The computing device 120 may be a computing system that includes a microprocessor 122, a memory 124, and various other components. An example of such a computing system 120 is disclosed in FIG. 7 below. In a method disclosed herein, the memory 124 may be used to store the sequence of input signals 110 generated by the pulse oximeter 104, the sequence of $SpO_2$ levels generated by the pulse oximeter 104, as well as various feature matrices 140 generated based on the sequence of input signals 110. For example, a feature matrix generator 130 may be used to generate the feature matrices 140 based on the sequence of input signals 110.

Such feature matrices 140 may include a feature matrix that represents maximum slopes of PPG pulse, the steepness of a PPG signal, skew of the PPG signal, the normalized amplitude of PPG pulse, maximum curvature of the PPG pulses, etc. For example, the feature matrix generator 130 may determine the maximum positive slope for a predetermined number of PPG pulses and generate a matrix of such maximum positive slopes. Alternatively, the feature matrix generator 130 may determine the maximum negative slope before dicrotic notches for a predetermined number of PPG pulses and generate a matrix of such maximum negative slopes. Another example of a feature matrix may be a feature matrix of maximum peak-to-peak amplitudes for a predetermined number of PPG pulses. In an alternative implementation, one or more feature matrices based on combination of the feature matrices discussed above may also be generated. In another alternative implementation, the feature matrices 140 may also include a matrix of the original PPG signal itself.

A graph 150 discloses oxygen saturation levels 170 in percentages against time. A saturation monitor module 132 monitors the oxygen saturation levels 170 as compared to a desaturation alarm threshold 152. For example, the desaturation alarm threshold 152 may be set to be at 90% oxygen saturation. As indicated in graph 150, the oxygen saturation levels 170 may cross the desaturation alarm threshold 152 at point A 160 to indicate onset of a desaturation event. Such desaturation event may be an SDE as indicated by a line 174 or may be a non-SDE as indicated by a line 172. For example, line 174 is considered to indicate an SDE due to the amount of the time L1 the oxygen saturation level is below the desaturation alarm threshold 152. Alternatively, line 174 may also be considered to indicate an SDE due to the significant depth D1 of the oxygen saturation level below the desaturation alarm threshold 152. On the other hand, a line 172 may be considered a non-SDE due to the shorter amount of time L2 for which the oxygen saturation level is below the desaturation alarm threshold 152 and/or due to the lesser depth D2 of the oxygen saturation level below the desaturation alarm threshold 152.

Furthermore, line 174 also indicates the oxygen saturation levels dipping below a severity threshold 154. For example, the severity threshold may be at 75% oxygen saturation, thus indicating an SDE. Compared to that line 172 does not dip below the severity threshold 154, which may be indicative of a non-SDE. As discussed below, the oxygen level desaturation severity prediction system 100 allows predicting the severity level of the desaturation event in response to the oxygen saturation levels 170 crossing the alarm threshold 152 using AI.

The memory 124 may also store instructions of a neural network based classifier module 134 that can be executed using the micro-processor 122. The classifier module 134 may be used to analyze sequences of input signals 110 generated by the pulse oximeter 104, the sequence of $SpO_2$ levels generated by the pulse oximeter 104, as well as various feature matrices 140 generated based on the sequences of input signals 110—together these sequences are referred to herein as the classifier input sequences. In one implementation the classifier module 134 may be a deep neural network module that analyzes the classifier input sequences using a long short-term memory (LSTM) based layers to predict severity level of desaturation events based on analysis of the various classifier input sequences. Alternatively, the classifier module 134 may be a convolutional neural network (CNN), a recurrent neural network (RNN), etc.

The classifier module 134 may be configured to predict severity level of desaturation events based on analysis of the various classifier input sequences. For example, the classifier module 134 may predict the length of the desaturation event and/or the depth of the desaturation event over a predetermined future time period, starting at point A 160, to determine whether the desaturation event is going to be an SDE or a non-SDE. In one implementation, the classifier module 134 outputs the probability of the desaturation event is going to be an SDE or a non-SDE.

Such probability may be used to manage an alarm to a clinician. Specifically, the memory 124 may also have an alarm manager module 136 that is configured to manage generation of alarm based as the desaturation threshold is reached based on classification of the desaturation event being an SDE or a non-SDE. For example, the alarm manager module 136 may compare the probability output generated by the classifier module 134 to a threshold probability $P_{thresh}$ to change the length of time before an alarm is generated.

The $P_{thresh}$ may be set by a user of the oxygen level desaturation severity prediction system 100. Similarly, a default alarm delay time period may also be set by the user. If the alarm manager module 136 determines the probability of an SDE, output by the classifier module 134, is below the $P_{thresh}$, it leaves the alarm delay time period to the default value. However, if the alarm manager module 136 determines the probability of an SDE, output by the classifier module 134, is above the $P_{thresh}$, it alters the alarm delay time period to below the default value.

As an example, the alarm delay may be set by default at 5, 10, or 20 seconds after crossing the desaturation alarm threshold 152. Then for a probability of an SDE>$P_{Thresh}$ the alarm delay may be reduced to zero or near zero. Alternatively, in such a case, if the alarm were originally set at 20 seconds delay, the delay may be reduced to 10 or 5 seconds. On the other hand, if a high probability of a non-SDE>$P_{Thresh}$ is exhibited, the alarm delay could be increased to for example 30, 60, 90 seconds or more. In one implementation, the probability of the desaturation event being SDE or non-SDE may be obtained from the classifier module 134 prior to final classification of the desaturation event as being SDE or non-SDE. Furthermore, the probability of the desaturation event being SDE or non-SDE may be linked to the alarm delay through a non-linear function as further discussed below in FIG. 4.

In one implementation, the alarm generation module 134 may provide an alarm management user interface (UI) to a user that allows the user to control how quickly the alarm is generated after the saturation levels crossing the desaturation alarm threshold 152. For example, such alarm management UI may allow the user to set the slope of the non-linear function linking the probability of the desaturation event being SDE or non-SDE to the alarm delay.

Figure 2:
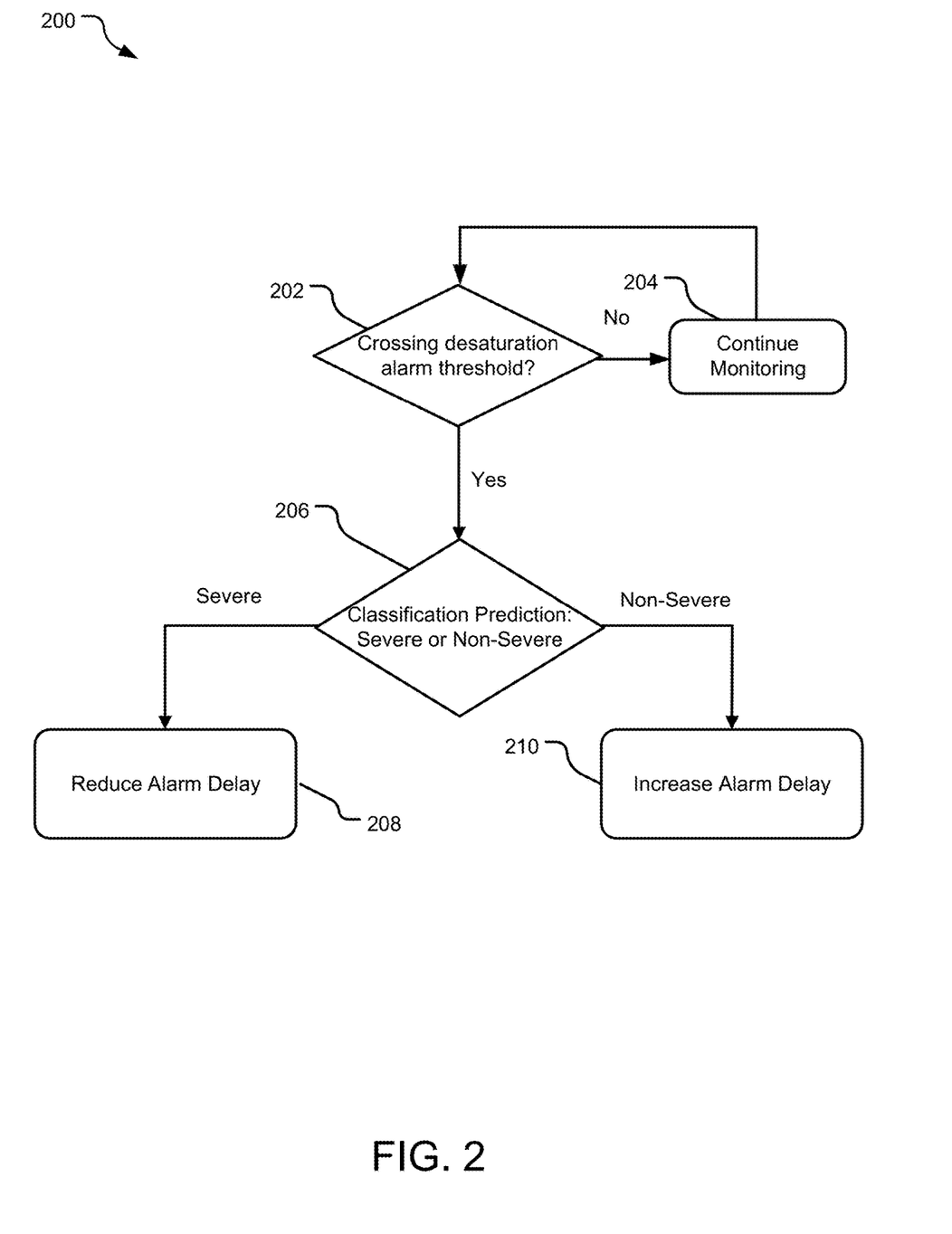
FIG. 2 illustrates example operations for managing alarm delay based on oxygen level desaturation severity predictions.

FIG. 2 illustrates example operations 200 for managing alarm delay based on oxygen level desaturation severity predictions. Specifically, one or more of the operations 200 may be implemented by computer executable instructions stored in the alarm manager module 136. An operation 202 determines if the oxygen saturation levels have crossed the desaturation alarm threshold to dip below the desaturation alarm threshold. If the oxygen saturation levels have not crossed the desaturation alarm threshold to dip below the desaturation alarm threshold, an operation 204 continues monitoring the oxygen saturation levels compared to the desaturation alarm threshold.

If the oxygen saturation levels have crossed the desaturation alarm threshold to dip below the desaturation alarm threshold, an operation 206 reviews the predicted classification of the desaturation event. For example, the operation 206 may review such classification from a neural network based classifier such as the classifiers disclosed below in FIGS. 5 and 6. If the desaturation event is classified as being an SDE, an operation 208 reduces the alarm delay so that the alarm may be generated relatively quickly after the saturation levels crossing the desaturation alarm threshold. On the other hand, if the desaturation event is classified as being a non-SDE, an operation 210 increases the alarm delay so that the alarm may be generated relatively later after the saturation levels crossing the desaturation alarm threshold.

Figure 3:
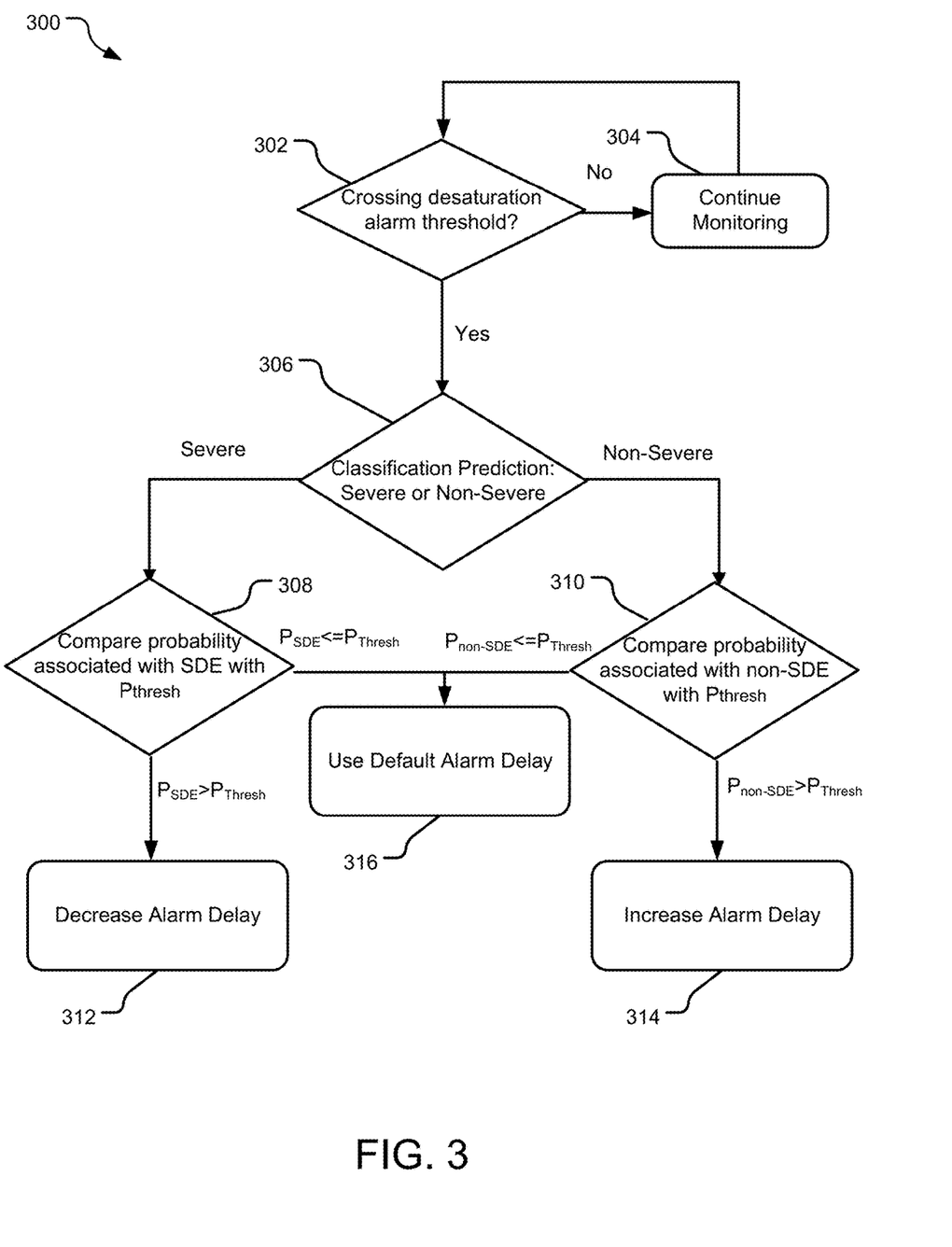
FIG. 3 illustrates example operations for managing alarm delay based on probabilities of oxygen level desaturation severity.

FIG. 3 illustrates example operations 300 for managing alarm delay based on probability of oxygen level desaturation severity. Specifically, one or more of the operations 300 may be implemented by computer executable instructions stored in the alarm manager module 136. An operation 302 determines if the oxygen saturation levels have crossed the desaturation alarm threshold to dip below the desaturation alarm threshold. If the oxygen saturation levels have not crossed the desaturation alarm threshold to dip below the desaturation alarm threshold, an operation 304 continues monitoring the oxygen saturation levels compared to the desaturation alarm threshold.

If the oxygen saturation levels have crossed the desaturation alarm threshold to dip below the desaturation alarm threshold, an operation 306 reviews the predicted classification of the desaturation event. For example, the operation 306 may review such classification from a neural network based classifier such as the classifiers disclosed below in FIGS. 5 and 6. If the desaturation event is classified as being an SDE, an operation 308 compares the probability $P_{SDE}$ associated with the SDE with the $P_{thresh}$. If $P_{SDE}>P_{thresh}$, an operation 312 decreases the alarm delay, resulting an alarm generation relatively sooner after the saturation levels cross the desaturation alarm threshold. On the other hand, if $P_{SDE} \leq P_{thresh}$, an operation 316 uses the default alarm delay.

On the other hand, if the desaturation event is classified as being a non-SDE, an operation 310 compares the probability $P_{non-SDE}$ associated with the non-SDE with the $P_{thresh}$. If $P_{non-SDE} > P_{thresh}$, an operation 314 increases the alarm delay, resulting an alarm generation relatively later after the saturation levels cross the desaturation alarm threshold. On the other hand, if $P_{non-SDE} \leq P_{thresh}$, the operation 316 uses the default alarm delay.

Figure 4:
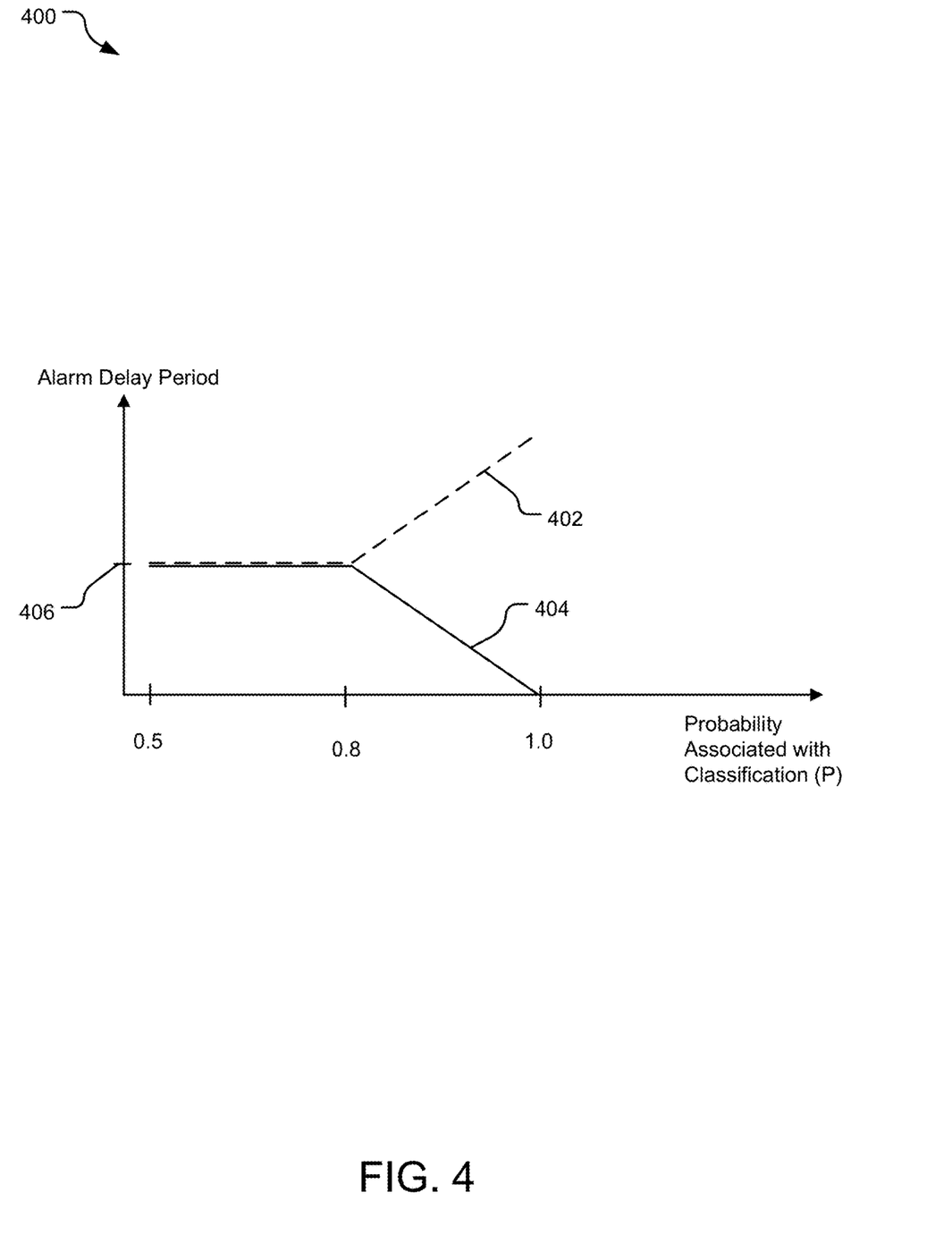
FIG. 4 illustrates an example graph indicating alarm delay based on probability associated with classification of an oxygen level desaturation event.

FIG. 4 illustrates an example graph 400 indicating alarm delay based on probability associated with classification of an oxygen level desaturation event. Specifically, the graph 400 illustrates how the probability (P) associated with classification of an oxygen level desaturation event itself may be linked to the delay period through a linear or nonlinear function. Here the alarm delay period remains at the default level 406 until P reaches a threshold value, which is set to be at 0.8 in this illustration. Thereafter, if a severe event is predicted, thus P being $P_{SDE}$, the alarm delay period is reduced to zero as a linear function of the probability P as indicated by 404. On the other hand, if a non-severe event is predicted, thus P being $P_{non-SDE}$, the alarm delay period is increased to a maximum value as a linear function of the probability P as indicated by 402. The functions 402 and 404 depicted in FIG. 4 are piecewise linear functions. However, these functions may also be continuous and/or non-linear. Furthermore, the threshold for the delay period default (0.8) may be altered to any number between 0.5 and 1.0.

In the above disclosed implementation, it is assumed that the prediction of the desaturation event is made as the saturation level crosses the desaturation alarm threshold. However, alternatively, the prediction of the desaturation event and its associated probability may be calculated continuously subsequent to the saturation level crossing the desaturation alarm threshold. This results in continuous updating of the prediction and resulting action regarding the alarm generation. For example, a non-SDE classification at threshold crossing may be updated to an SDE classification after a time period below the threshold, in which case the alarm could be sounded immediately.

Furthermore, the above illustrations use a fixed criterion for an SDE as a second fixed threshold below the desaturation alarm threshold (e.g. 90%). This second fixed threshold may be set at, e.g., 15 saturation percentage points below the desaturation alarm threshold. However, an alternative implementation may use alternative criteria for severity including a drop below a baseline level for the patient. For example, a patient may have a baseline level of 87% and a severe desaturation may be defined as a 15% drop below this level (e.g. at 72% saturation).

Figure 5:
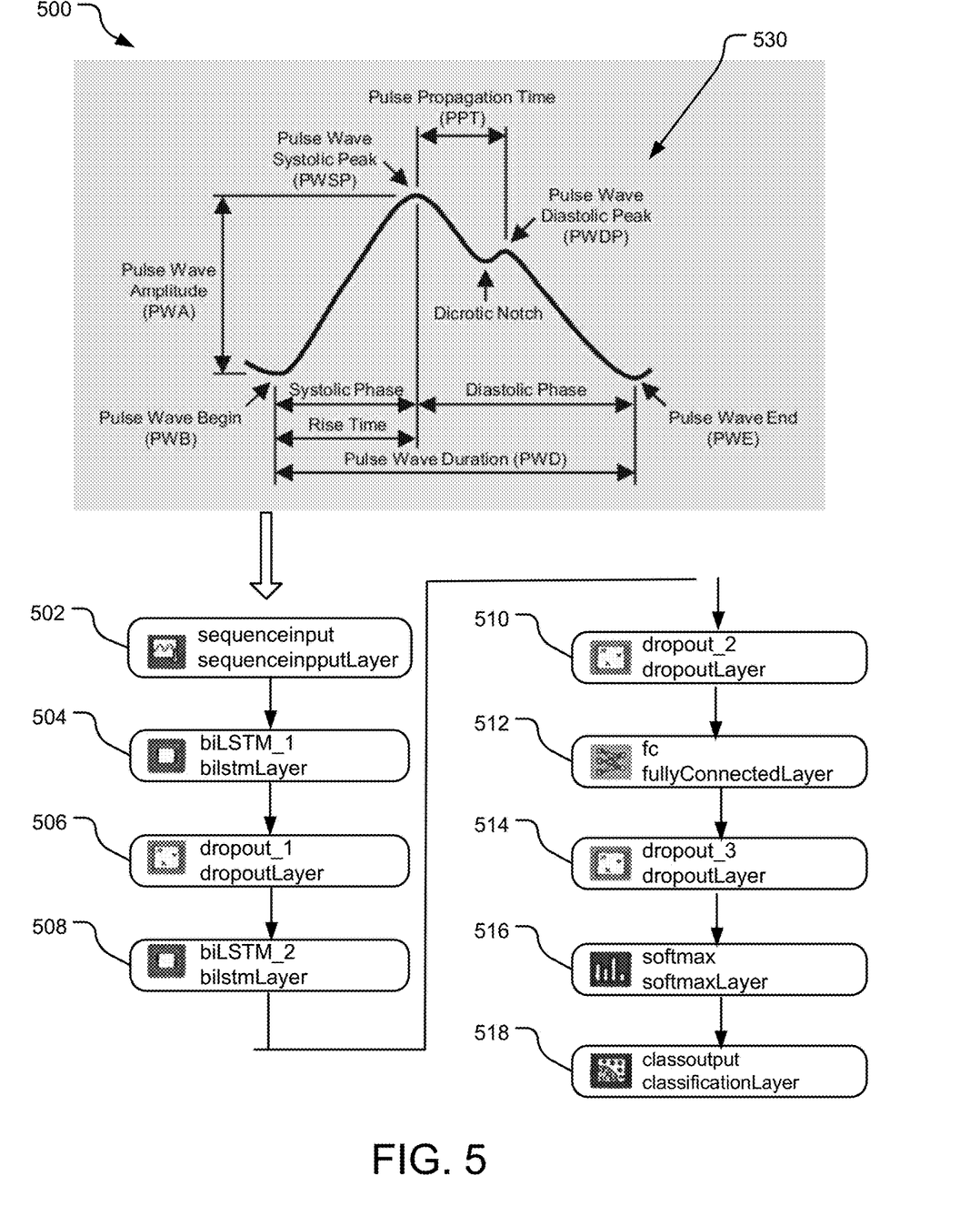
FIG. 5 illustrates an example long short-term memory (LSTM) architecture used as the classifier for the oxygen level desaturation severity prediction system disclosed herein.

The AI method used by the classifier may consist of, for example, a deep learning model, including a convolutional neural network (CNN) or a long-short term memory network (LSTM). FIG. 5 illustrates an example deep learning LSTM network 500 used as the classifier for the oxygen level desaturation severity prediction system disclosed herein. Specifically, one or more layers of the LTSM architecture 500 may be implemented by computer executable instructions stored in the classifier module 134. The LSTM network 500 may include multiple layers 502-518. The LSTM network 500 may be trained on historic data sets where both severe and non-severe desaturation events are present.

The LSTM network 500 may be trained on the original PPG signals (red and infrared, such as the signal 110a, 110b illustrated in FIG. 1), the calculated $SpO_2$ values by the oximeter 102, the heart rate calculated by the oximeter 102, and/or other feature matrices 140 derived from the PPG signal, etc. An example PPG pulse 530 discloses various PPG pulse parameters that may be used to generate input features for the LSTM network 500. For example, the feature matrices 140 derived from the PPG signal may include: skew of the pulses, amplitude of the pulses, normalized amplitude of the pulses, maximum slope of the PPG pulse 530, the maximum curvature of the PPG pulse 530, the location of maximum slope, curvature, and other morphological parameters derived from the PPG pulse 530.

In the illustrated implementation of the LSTM network 500, the class output layer 518 may output the classification of the desaturation event being SDE or non-SDE. However, an intermediate layer, such as the softmax layer may output the probabilities associated with the desaturation events being SDE or non-SDE.

Figure 6:
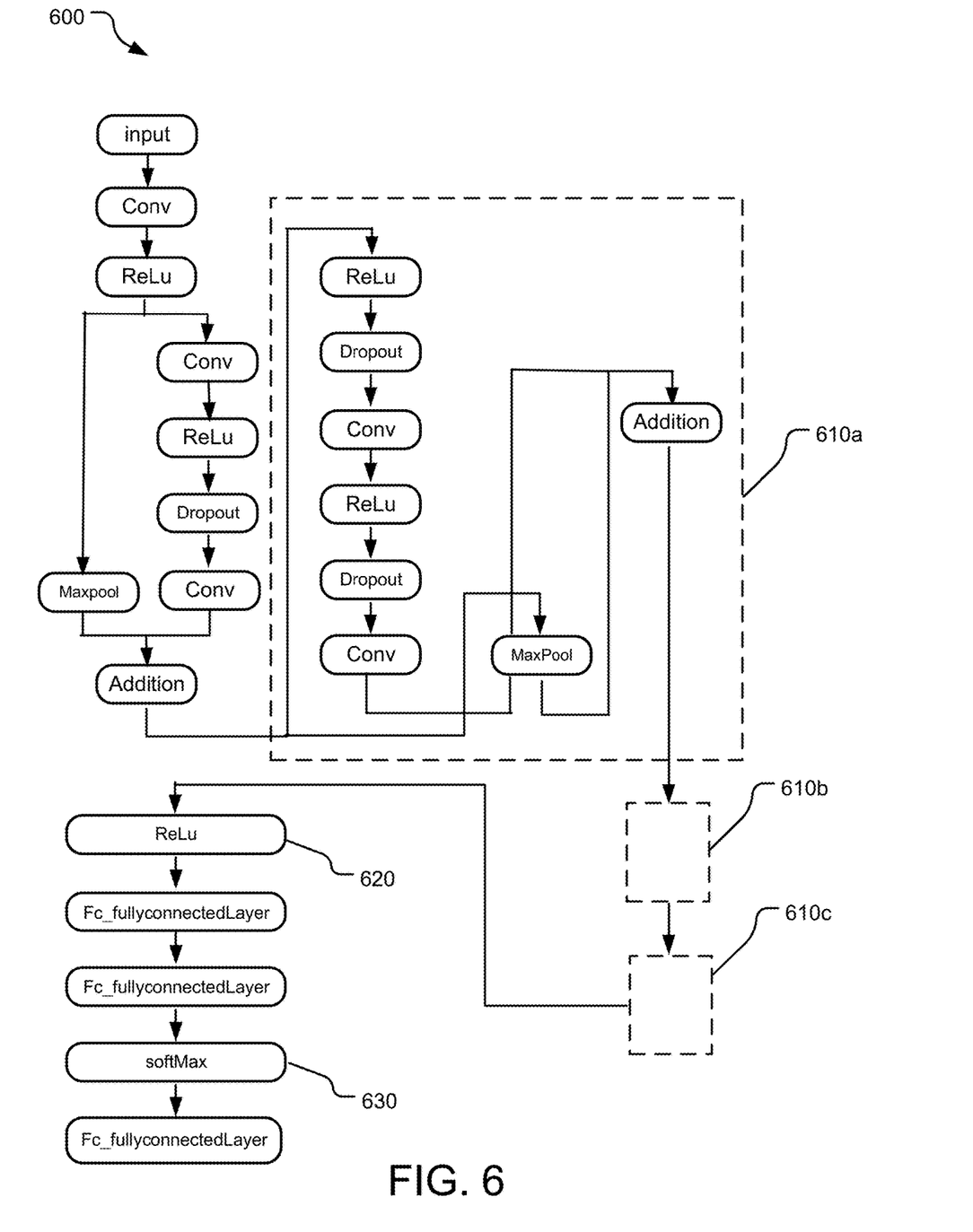
FIG. 6 illustrates an example neural network architecture used as the classifier for the oxygen level desaturation severity prediction system disclosed herein.

FIG. 6 illustrates an example convolutional neural network (CNN) 600 used as the classifier for the oxygen level desaturation severity prediction system disclosed herein. Specifically, one or more layers of the CNN 600 may be implemented by computer executable instructions stored in the classifier module 134. The CNN 600 may be a residual neural network (ResNet) that builds on constructs known from pyramidal cells by utilizing shortcuts to jump over some layers. The CNN 600 is illustrated as made of repeating blocks 610a, 610b, which may be repeated an arbitrary number of times. Furthermore, specific parameters of each convolution, such as stride (controlling how a filter convolves around an input volume), padding (adding zeros to input matrix), etc., can be tuned. In the illustrated implementation, there are two (2) fully connected layers between the ReLu layer 620 and the softmax payer 630. However, alternative implementations may include, n (n>1) number of fully connected layers between the ReLu layer 620 and the softmax payer 630.

Figure 7:
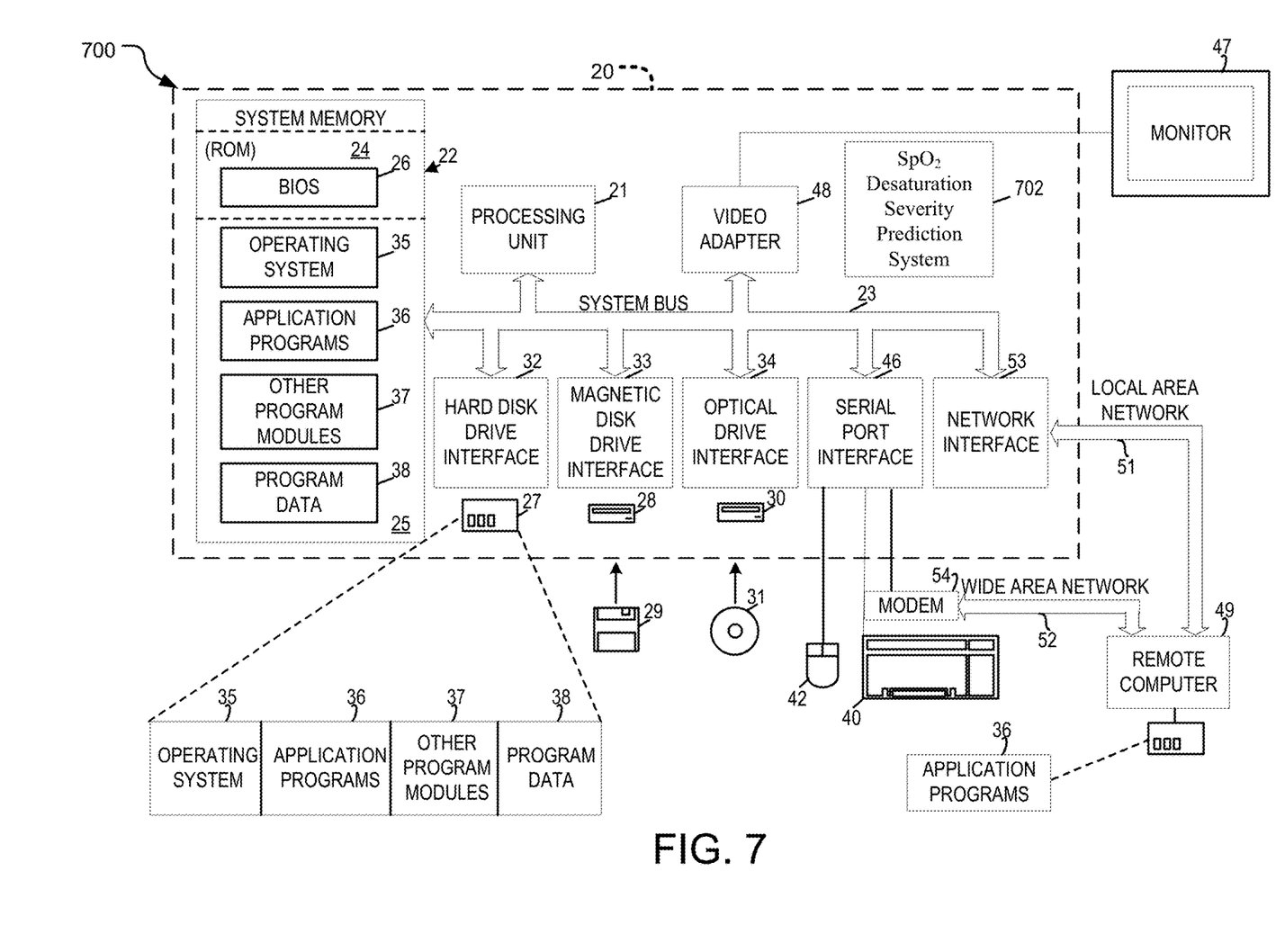
FIG. 7 illustrates an example computing system that may be useful in implementing the described technology.

FIG. 7 illustrates an example system 700 that may be useful in implementing the described technology for providing attestable and destructible device identity. The example hardware and operating environment of FIG. 7 for implementing the described technology includes a computing device, such as a general-purpose computing device in the form of a computer 20, a mobile telephone, a personal data assistant (PDA), a tablet, smart watch, gaming remote, or other type of computing device. In the implementation of FIG. 7, for example, the computer 20 includes a processing unit 21, a system memory 22, and a system bus 23 that operatively couples various system components including the system memory to the processing unit 21. There may be only one or there may be more than one processing unit 21, such that the processor of the computer 20 comprises a single central-processing unit (CPU), or a plurality of processing units, commonly referred to as a parallel processing environment. The computer 20 may be a conventional computer, a distributed computer, or any other type of computer; the implementations are not so limited.

The system bus 23 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 24 and random-access memory (RAM) 25. A basic input/output system (BIOS) 26, containing the basic routines that help to transfer information between elements within the computer 20, such as during start-up, is stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other storage media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated tangible computer-readable media provide non-volatile storage of computer-readable instructions, data structures, program modules and other data for the computer 20. It should be appreciated by those skilled in the art that any type of tangible computer-readable media may be used in the example operating environment.

A number of program modules may be stored on the hard disk drive 27, magnetic disk 28, optical disk 30, ROM 24, or RAM 25, including an operating system 35, one or more application programs 36, other program modules 37, and program data 38. A user may generate reminders on the personal computer 20 through input devices such as a keyboard 40 and pointing device 42. Other input devices (not shown) may include a microphone (e.g., for voice input), a camera (e.g., for a natural user interface (NUI)), a joystick, a game pad, a satellite dish, a scanner, or the like. These and other input devices are often connected to the processing unit 21 through a serial port interface 46 that is coupled to the system bus 23, but may be connected by other interfaces, such as a parallel port, game port, or a universal serial bus (USB) (not shown). A monitor 47 or other type of display device is also connected to the system bus 23 via an interface, such as a video adapter 48. In addition to the monitor, computers typically include other peripheral output devices (not shown), such as speakers and printers.

The computer 20 may operate in a networked environment using logical connections to one or more remote computers, such as remote computer 49. These logical connections are achieved by a communication device coupled to or a part of the computer 20; the implementations are not limited to a particular type of communications device. The remote computer 49 may be another computer, a server, a router, a network PC, a client, a peer device or other common network node, and typically includes many or all of the elements described above relative to the computer 20. The logical connections depicted in FIG. 7 include a local-area network (LAN) 51 and a wide-area network (WAN) 52. Such networking environments are commonplace in office networks, enterprise-wide computer networks, intranets and the Internet, which are all types of networks.

When used in a LAN-networking environment, the computer 20 is connected to the local network 51 through a network interface or adapter 53, which is one type of communications device. When used in a WAN-networking environment, the computer 20 typically includes a modem 54, a network adapter, a type of communications device, or any other type of communications device for establishing communications over the wide area network 52. The modem 54, which may be internal or external, is connected to the system bus 23 via the serial port interface 46. In a networked environment, program engines depicted relative to the personal computer 20, or portions thereof, may be stored in the remote memory storage device. It is appreciated that the network connections shown are examples and other means of communications devices for establishing a communications link between the computers may be used.

In an example implementation, software or firmware instructions for providing attestable and destructible device identity may be stored in memory 22 and/or storage devices 29 or 31 and processed by the processing unit 21. One or more datastores disclosed herein may be stored in memory 22 and/or storage devices 29 or 31 as persistent datastores. For example, an $SpO_2$ desaturation severity prediction system 702 (illustrated within the personal computer 20) may be implemented on the computer 20 (alternatively, the $SpO_2$ desaturation severity prediction system 702 may be implemented on a server or in a cloud environment). The $SpO_2$ desaturation severity prediction system 702 may utilize one of more of the processing unit 21, the memory 22, the system bus 23, and other components of the personal computer 20.

In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless communication methods.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A method, comprising:
   comparing an input sequence of oxygen saturation levels of a patient to a desaturation alarm threshold to determine a desaturation event;
   generating an input feature matrix based on the input sequence of oxygen saturation levels;
   inputting the input feature matrix to a neural network; and
   classifying, using the neural network based on the input feature matrix, the desaturation event as being a severe desaturation event (SDE) or a non-severe desaturation event (non-SDE).

2. The method of claim 1, wherein the input sequence of oxygen saturation levels is generated based on an input signal sequence indicative of a physiological condition of the patient, the classifying the desaturation event further comprising:

using the neural network, predicting a length of the desaturation event starting from an onset of the desaturation event; and classifying the desaturation event based on the predicted length of the desaturation event.

3. The method of claim 1, the classifying the desaturation event further comprising:

using the neural network, predicting a depth of the desaturation event starting from an onset of the desaturation event; and classifying the desaturation event based on the predicted depth of the desaturation event.

4. The method of claim 1, further comprising reducing an alarm delay in response to classifying the desaturation event as being an SDE.

5. The method of claim 1, further comprising increasing an alarm delay in response to classifying the desaturation event as being a non-SDE.

6. The method of claim 1, further comprising generating, using the neural network based on the input feature matrix, a probability associated with the desaturation event being an SDE or a non-SDE.

7. The method of claim 6, further comprising:

comparing the probability associated with the desaturation event being an SDE or a non-SDE with a threshold probability; and adjusting an alarm delay in response to the comparison.

8. The method of claim 7, wherein adjusting the alarm delay further comprises adjusting the alarm delay based on a non-linear function of the probability associated with the desaturation event.

9. The method of claim 1, wherein the neural network is at least one of a convolutional neural network (CNN) and a long short-term memory (LSTM) neural network.

10. The method of claim 1, wherein the input feature matrix is one of a matrix of maximum slopes of PPG pulses, a matrix of steepness of PPG pulses, a matrix of normalized amplitudes of PPG pulses, a matrix of maximum curvatures of PPG pulses, or a matrix of maximum negative slopes before dicrotic notches of PPG pulses.

11. In a computing environment, a method performed at least in part on at least one processor, the method comprising:

comparing an input sequence of oxygen saturation levels of a patient to a desaturation alarm threshold to determine a desaturation event;

generating an input feature matrix based on the input sequence of oxygen saturation levels;

inputting the input feature matrix to a neural network;

classifying, using the neural network based on the input feature matrix, the desaturation event as being a severe desaturation event (SDE) or a non-severe desaturation event (non-SDE); and adjusting an alarm delay in response to classifying the desaturation event as being an SDE or a non-SDE.

12. The method of claim 11, wherein the input sequence of oxygen saturation levels is generated based on an input signal sequence indicative of a physiological condition of the patient, the classifying the desaturation event further comprising:

using the neural network, predicting at least one of a length or a depth of the desaturation event starting from an onset of the desaturation event; and classifying the desaturation event based on the at least one of the predicted length or predicted depth of the desaturation event.

13. The method of claim 11, wherein adjusting the alarm delay further comprises reducing the alarm delay in response to classifying the desaturation event as being an SDE.

14. The method of claim 11, wherein adjusting the alarm delay further comprises increasing the alarm delay in response to classifying the desaturation event as being a non-SDE.

15. The method of claim 11, further comprising:

generating, using the neural network based on the input feature matrix, a probability associated with the desaturation event being an SDE or a non-SDE;

comparing the probability associated with the desaturation event being an SDE or a non-SDE with a threshold probability; and adjusting the alarm delay in response to the comparison.

16. The method of claim 15, wherein adjusting the alarm delay further comprises adjusting the alarm delay based on a non-linear function of the probability associated with the desaturation event.

17. The method of claim 11, wherein the input feature matrix is one of a matrix of maximum slopes of PPG pulses, a matrix of steepness of PPG pulses, a matrix of normalized amplitudes of PPG pulses, a matrix of maximum curvatures of PPG pulses, or a matrix of maximum negative slopes before dicrotic notches of PPG pulses.

18. A physical article of manufacture including one or more tangible computer-readable storage media, encoding computer-executable instructions for executing on a computer system a computer process to provide an automated connection to a collaboration event for a computing device, the computer process comprising:

comparing an input sequence of oxygen saturation levels of a patient to a desaturation alarm threshold to determine a desaturation event;

generating an input feature matrix based on the input sequence of oxygen saturation levels;

inputting the input feature matrix to a neural network;

classifying, using the neural network based on the input feature matrix, the desaturation event as being a severe desaturation event (SDE) or a non-severe desaturation event (non-SDE); and adjusting an alarm delay in response to classifying the desaturation event as being an SDE or a non-SDE.

19. The physical article of manufacture of claim 18, wherein the input sequence of oxygen saturation levels is generated based on an input signal sequence indicative of a physiological condition of the patient, the computer process further comprising:

generating, using the neural network based on the input feature matrix, a probability associated with the desaturation event being an SDE or a non-SDE;

comparing the probability associated with the desaturation event being an SDE or a non-SDE with a threshold probability; and adjusting the alarm delay in response to the comparison.

20. The physical article of manufacture of claim 18, wherein the input feature matrix is one of a matrix of maximum slopes of PPG pulses, a matrix of steepness of PPG pulses, a matrix of normalized amplitudes of PPG pulses, a matrix of maximum curvatures of PPG pulses, or a matrix of maximum negative slopes before dicrotic notches of PPG pulses.

* * * * *